(12) United States Patent
Gross

(10) Patent No.: US 8,923,973 B2
(45) Date of Patent: Dec. 30, 2014

(54) BLOOD FLOW CONTROL ELEMENT

(75) Inventor: Yossi Gross, Moshav Mazor (IL)

(73) Assignee: Rainbow Medical Ltd., Herzliya (IL)

( * ) Notice: Subject to any disclaimer, the term of this patent is extended or adjusted under 35 U.S.C. 154(b) by 378 days.

(21) Appl. No.: 13/293,736

(22) Filed: Nov. 10, 2011

(65) Prior Publication Data

US 2013/0123569 A1 May 16, 2013

(51) Int. Cl.
*A61B 5/02* (2006.01)
*A61B 17/135* (2006.01)
*A61M 1/12* (2006.01)
*A61F 2/82* (2013.01)
*A61M 1/10* (2006.01)
*A61F 2/06* (2013.01)
*A61F 2/94* (2013.01)
*A61N 1/362* (2006.01)
*A61B 17/12* (2006.01)
*A61B 17/00* (2006.01)

(52) U.S. Cl.
CPC ........... *A61B 17/1355* (2013.01); *A61M 1/122* (2013.01); *A61M 1/125* (2013.01); *A61F 2/82* (2013.01); *A61M 1/10* (2013.01); *A61M 2205/3523* (2013.01); *A61M 2205/3569* (2013.01); *A61F 2/06* (2013.01); *A61F 2/064* (2013.01); *A61F 2/94* (2013.01); *A61N 1/3627* (2013.01); *A61F 2002/068* (2013.01); *A61F 2250/0001* (2013.01); *A61B 17/12109* (2013.01); *A61B 2017/00221* (2013.01)
USPC .......................................................... 607/44

(58) Field of Classification Search
None
See application file for complete search history.

(56) References Cited

U.S. PATENT DOCUMENTS

| 4,546,759 | A | 10/1985 | Solar |
| 4,753,221 | A | 6/1988 | Kensey et al. |
| 4,943,277 | A | 7/1990 | Bolling |
| 5,304,208 | A | 4/1994 | Inguaggiato et al. |
| 5,454,838 | A | 10/1995 | Vallana et al. |
| 5,509,428 | A | 4/1996 | Dunlop |
| 5,540,733 | A | 7/1996 | Testerman et al. |
| 5,549,655 | A | 8/1996 | Erickson |
| 5,591,216 | A | 1/1997 | Testerman et al. |
| 5,800,375 | A | 9/1998 | Sweezer et al. |
| 5,810,757 | A | 9/1998 | Sweezer, Jr. et al. |

(Continued)

FOREIGN PATENT DOCUMENTS

| WO | 2004/064729 | 8/2004 |
| WO | 2004/073796 | 9/2004 |
| WO | 2007/083288 | 7/2007 |
| WO | 2012/066532 | 5/2012 |

OTHER PUBLICATIONS

C. de Balthasar, G. Cosendai, M. Hansen, D. Canfield, L. Chu, R. Davis, and J. Schulman, "Attachment of leads to RF-BION® microstimulators.".

(Continued)

*Primary Examiner* — Carl H Layno
*Assistant Examiner* — Jon Eric C Morales

(57) ABSTRACT

Apparatus for treating obstructive blood flow disorders, is provided, including (1) an external device, configured for placement outside of a body of a subject and to sense a factor of the subject, and to generate a signal in response to the sensed factor, and (2) an implant, which comprises a wireless receiver for receiving the signal, and an effector element, the implant configured and positioned to alter a blood flow of the subject in response to the signal.

23 Claims, 8 Drawing Sheets

(56) References Cited

U.S. PATENT DOCUMENTS

| | | | |
|---|---|---|---|
| 5,944,680 | A | 8/1999 | Christopherson |
| 6,086,527 | A | 7/2000 | Talpade |
| 6,139,487 | A | 10/2000 | Siess |
| 6,212,435 | B1 | 4/2001 | Lattner et al. |
| 6,240,316 | B1 | 5/2001 | Richmond et al. |
| 6,277,078 | B1 | 8/2001 | Porat et al. |
| 6,345,202 | B2 | 2/2002 | Richmond et al. |
| 6,459,928 | B2 | 10/2002 | Mika et al. |
| 6,508,777 | B1 | 1/2003 | Macoviak et al. |
| 6,602,270 | B2 | 8/2003 | Leschinsky et al. |
| 6,618,627 | B2 | 9/2003 | Lattner et al. |
| 6,641,542 | B2 | 11/2003 | Cho et al. |
| 6,733,459 | B1 | 5/2004 | Atsumi |
| 6,770,022 | B2 | 8/2004 | Mechlenburg |
| 7,025,730 | B2 | 4/2006 | Cho et al. |
| 7,056,336 | B2 | 6/2006 | Armstrong et al. |
| 7,159,593 | B2 | 1/2007 | McCarthy et al. |
| 7,167,748 | B2 | 1/2007 | Ben-Haim et al. |
| 7,277,749 | B2 | 10/2007 | Gordon et al. |
| 7,476,200 | B2 | 1/2009 | Tal |
| 7,483,743 | B2 | 1/2009 | Mann et al. |
| 7,660,632 | B2 | 2/2010 | Kirby et al. |
| 7,680,538 | B2 | 3/2010 | Durand et al. |
| 7,706,884 | B2 | 4/2010 | Libbus |
| 7,734,348 | B2 | 6/2010 | Zhang et al. |
| 7,765,000 | B2 | 7/2010 | Zhang et al. |
| 7,797,050 | B2 | 9/2010 | Libbus et al. |
| 7,853,305 | B2 | 12/2010 | Simon et al. |
| 8,070,708 | B2 | 12/2011 | Rottenberg et al. |
| 2002/0103501 | A1 | 8/2002 | Diaz et al. |
| 2002/0169413 | A1 | 11/2002 | Keren et al. |
| 2004/0010303 | A1 | 1/2004 | Bolea et al. |
| 2004/0019368 | A1 | 1/2004 | Lattner et al. |
| 2004/0064090 | A1 | 4/2004 | Keren et al. |
| 2004/0111006 | A1 | 6/2004 | Alferness et al. |
| 2004/0162514 | A1 | 8/2004 | Alferness et al. |
| 2005/0148925 | A1 | 7/2005 | Rottenberg et al. |
| 2005/0165457 | A1 | 7/2005 | Benser et al. |
| 2005/0245893 | A1 | 11/2005 | Leschinsky |
| 2006/0064059 | A1 | 3/2006 | Gelfand et al. |
| 2006/0206029 | A1 | 9/2006 | Yair |
| 2006/0217588 | A1 | 9/2006 | Gross et al. |
| 2007/0005010 | A1 | 1/2007 | Mori et al. |
| 2007/0038261 | A1 | 2/2007 | Kieval et al. |
| 2007/0083258 | A1 | 4/2007 | Falotico et al. |
| 2007/0100430 | A1 | 5/2007 | Rudakov et al. |
| 2007/0173893 | A1 | 7/2007 | Pitts |
| 2007/0191904 | A1* | 8/2007 | Libbus et al. ............ 607/44 |
| 2007/0274565 | A1 | 11/2007 | Penner |
| 2009/0030471 | A1 | 1/2009 | Rousso et al. |
| 2009/0112285 | A1 | 4/2009 | Cahan et al. |
| 2009/0118785 | A1 | 5/2009 | Ignagni et al. |
| 2009/0137968 | A1 | 5/2009 | Rottenberg |
| 2009/0177090 | A1 | 7/2009 | Grunwald et al. |
| 2010/0125310 | A1 | 5/2010 | Wilson et al. |
| 2010/0185255 | A1 | 7/2010 | Libbus |
| 2010/0222832 | A1 | 9/2010 | Zhang et al. |
| 2012/0123498 | A1 | 5/2012 | Gross |
| 2013/0123880 | A1* | 5/2013 | Dagan et al. ............ 607/61 |

OTHER PUBLICATIONS

D.W. Eisele, A.R. Schwartz, and P.L. Smith, "Tongue neuromuscular and direct hypoglossal nerve stimulation for obstructive sleep apnea.," *Otolaryngologic clinics of North America*, vol. 36, 2003, p. 501.

G.E. Loeb, F.J.R. Richmond, J. Singh, R.A. Peck, W. Tan, Q. Zou, and N. Sachs, "RF-powered BIONs™ for stimulation and sensing," *Engineering in Medicine and Biology Society, 2004. IEMBS'04. 26th Annual International Conference of the IEEE*, 2005, pp. 4182-4185.

G.E. Loeb, F.J. Richmond, and L.L. Baker, "The BION devices: injectable interfaces with peripheral nerves and muscles," *Neurosurgical focus*, vol. 20, 2006, pp. 1-9.

E.A. Mann, T. Burnett, S. Cornell, and C.L. Ludlow, "The effect of neuromuscular stimulation of the genioglossus on the hypopharyngeal airway," *The Laryngoscope*, vol. 112, 2002, pp. 351-356.

A. Oliven, R.P. Schnall, G. Pillar, N. Gavriely, and M. Odeh, "Sublingual electrical stimulation of the tongue during wakefulness and sleep," *Respiration physiology*, vol. 127, 2001, pp. 217-226.

A. Oliven, D.J. O'Hearn, A. Boudewyns, M. Odeh, W. De Backer, P. van de Heyning, P.L. Smith, D.W. Eisele, L. Allan, H. Schneider, and others, "Upper airway response to electrical stimulation of the genioglossus in obstructive sleep apnea," *Journal of Applied Physiology*, vol. 95, 2003, p. 2023.

A. Oliven, M. Odeh, L. Geitini, R. Oliven, U. Steinfeld, A.R. Schwartz, and N. Tov, "Effect of coactivation of tongue protrusor and retractor muscles on pharyngeal lumen and airflow in sleep apnea patients," *Journal of Applied Physiology*, vol. 103, 2007, p. 1662.

A. R. Schwartz, D W Eisele, A. Hari, R. Testerman, D. Erickson, and P.L. Smith, "Electrical stimulation of the lingual musculature in obstructive sleep apnea," *Journal of Applied Physiology*, vol. 81, 1996, p. 643.

W.H. Tran, G.E. Loeb, F.J.R. Richmond, A.C. Dupont, K.C. Mahutte, C.S.H. Sassoon, and M.J. Dickel, "Development of asynchronous, intralingual electrical stimulation to treat obstructive sleep apnea," *Engineering in Medicine and Biology Society, 2003. Proceedings of the 25th Annual International Conference of the IEEE*, 2004, pp. 375-378.

W.H. Tran, G.E. Loeb, F.J.R. Richmond, R. Ahmed, G.T. Clark, and P.B. Haberman, "First subject evaluated with simulated BION™ treatment in genioglossus to prevent obstructive sleep apnea," *Engineering in Medicine and Biology Society, 2004. IEMBS'04. 26th Annual International Conference of the IEEE*, 2005, pp. 4287-4289.

P.R. Troyk, "Injectable electronic identification, monitoring, and stimulation systems," *Biomedical Engineering*, vol. 1, 1999, p. 177.

T.K. Whitehurst, J.H. Schulman, K.N. Jaax, and R. Carbunaru, "The Bion® Microstimulator and its Clinical Applications," *Implantable Neural Prostheses 1*, 2009, pp. 253-273.

D.J. Young, "Wireless powering and data telemetry for biomedical implants," *Engineering in Medicine and Biology Society, 2009. EMBC 2009. Annual International Conference of the IEEE*, 2009, pp. 3221-3224.

Reid R. Harrison, et al., "Wireless Neural Recording with Single Low-Power Integrated Circuit", IEEE Trans Neural Syst Rehabil Eng. Aug. 2009; 17(4): 322-329.

An International Search Report and a Written Opinion both dated Apr. 17, 2012 which issued during the prosecution of Applicant's PCT/IL11/00870.

Patents Galore: Implantable Neurostimulators Fight Snoring and Corpse Eye-Proof Scanners. Printout from http://medgadget.com/2006/03/patents_galore.html (Downloaded Jan. 2012).

A heart pump without a cord, MIT Technology Review, Jul. 18, 2011 http://www.technologyreview.com/biomedicine/38064/.

An Office Action dated May 11, 2012, which issued during the prosecution of U.S. Appl. No. 12/946,246.

U.S. Appl. No. 60/541,267 to Rottenberg, filed Feb. 3, 2004.
U.S. Appl. No. 60/573,378 to Rottenberg, filed May 24, 2004.
U.S. Appl. No. 60/761,192 to Rozy, filed Jan. 23, 2006.
U.S. Appl. No. 60/862,496 to Levi, filed Oct. 23, 2006.
Office Action issued in U.S. Appl. No. 13/249,062, dated Dec. 13, 2013.

* cited by examiner

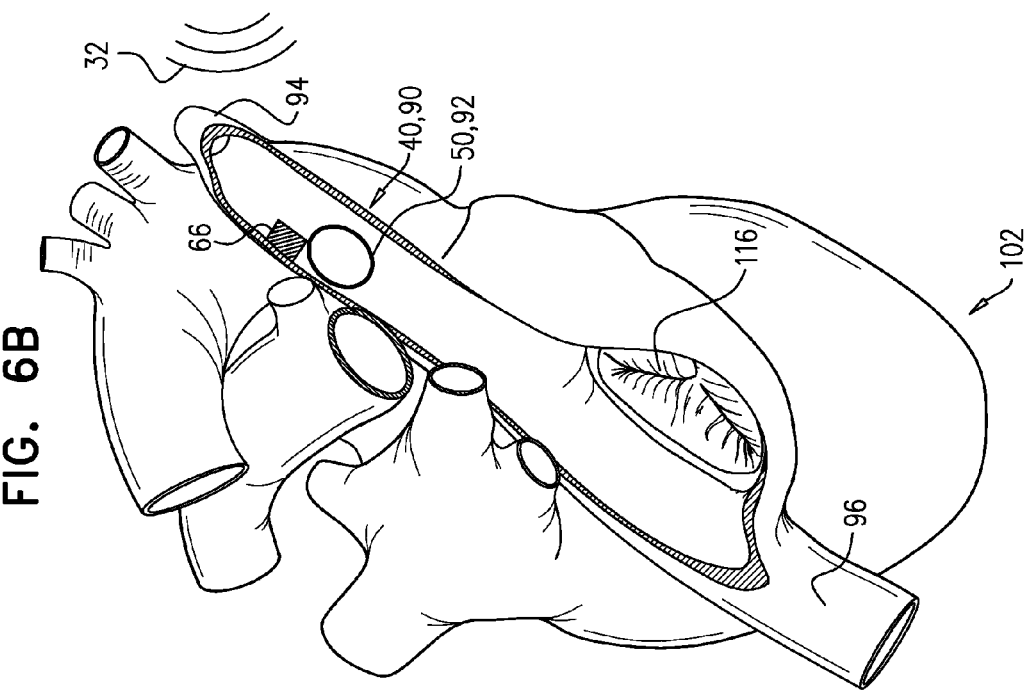
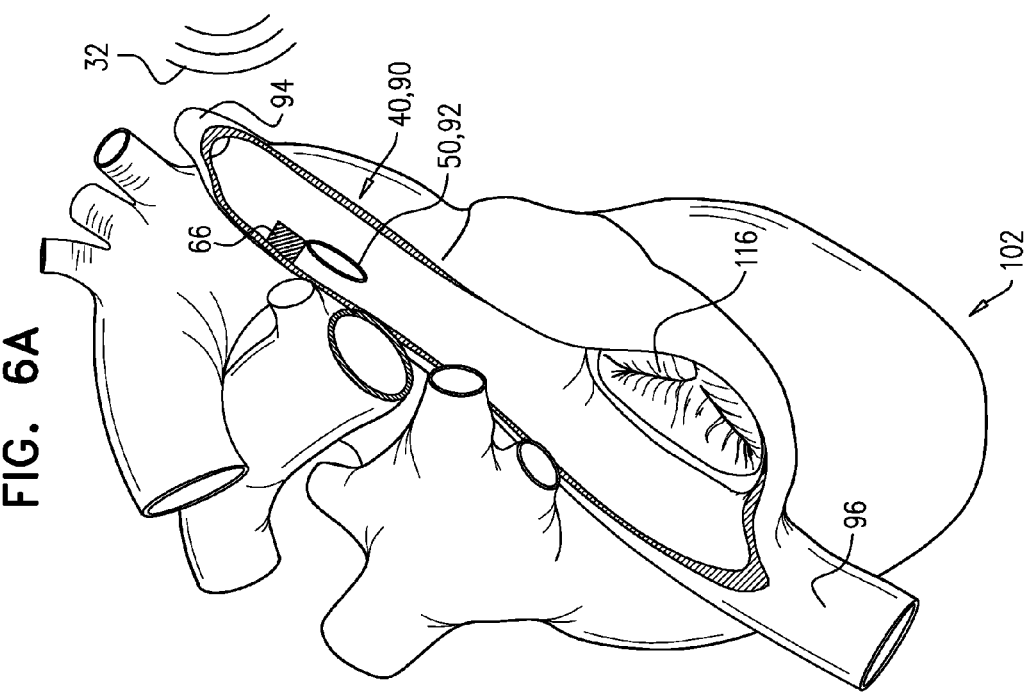

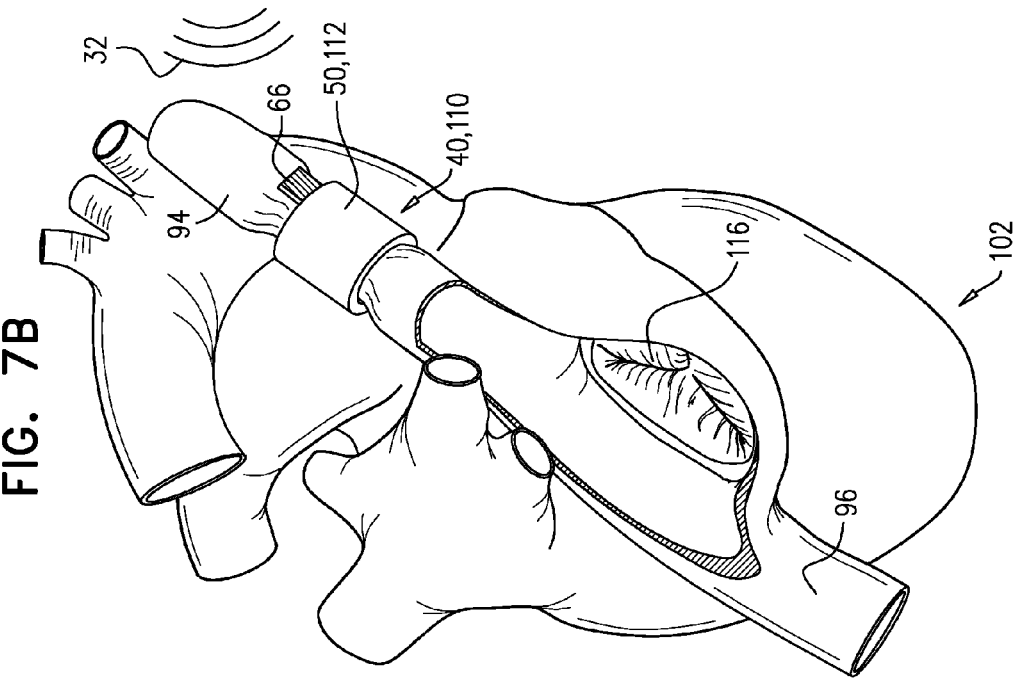
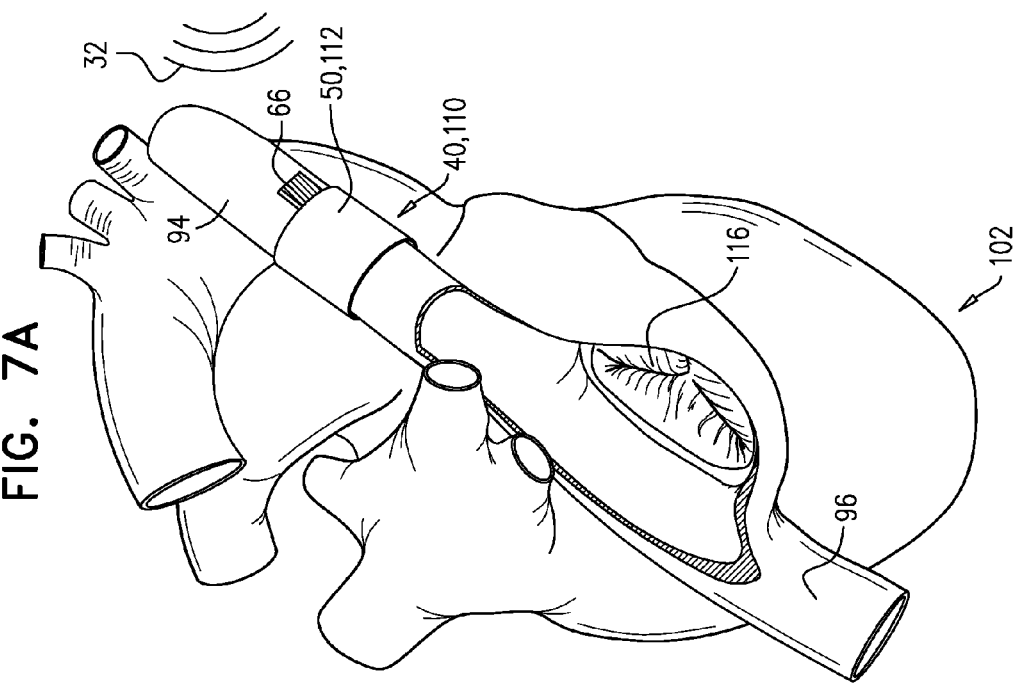

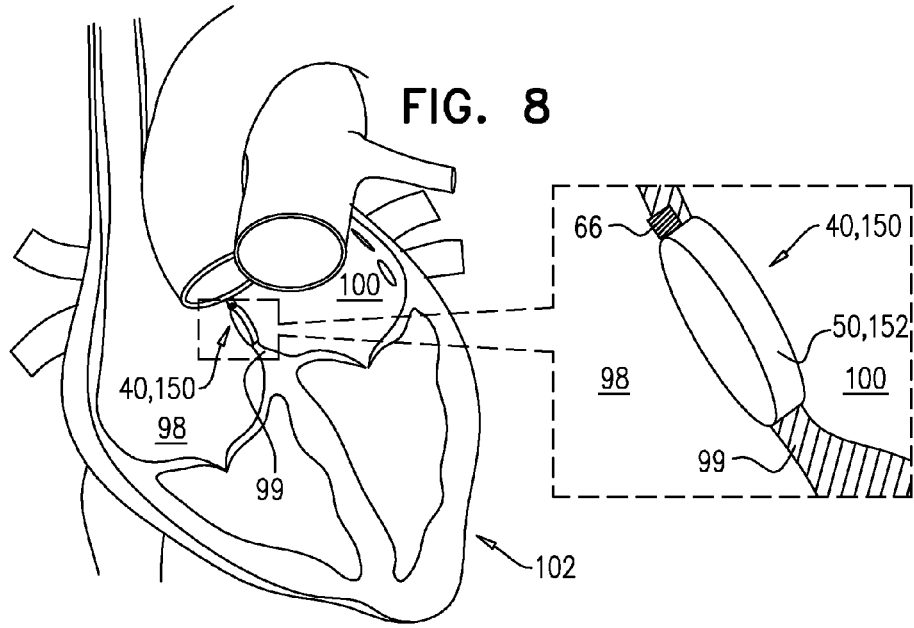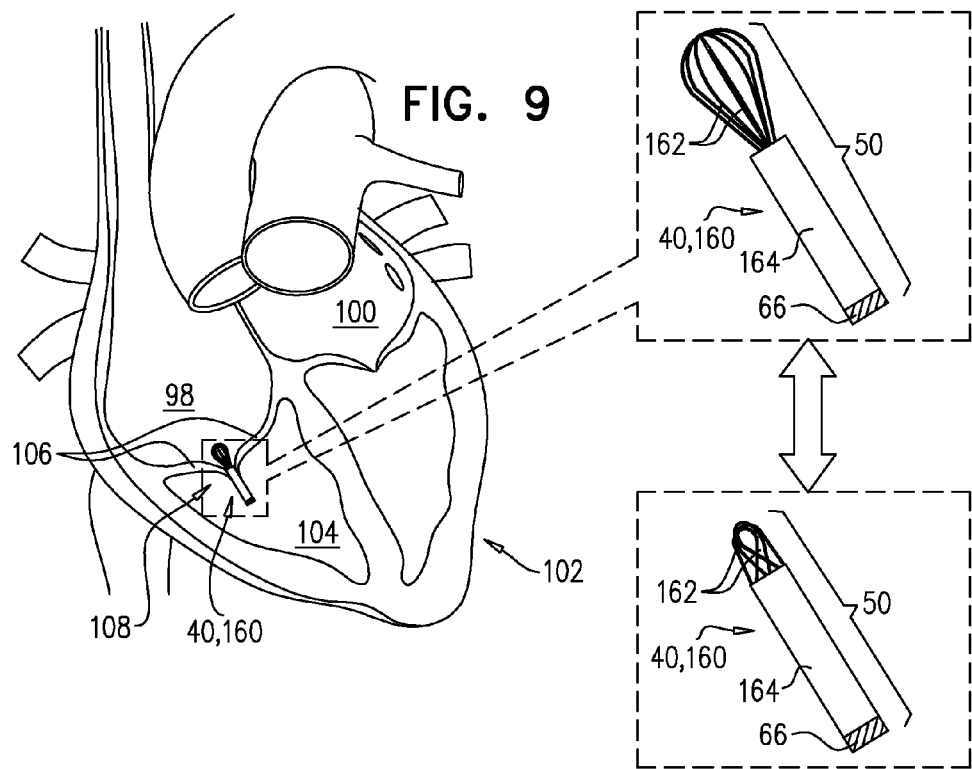

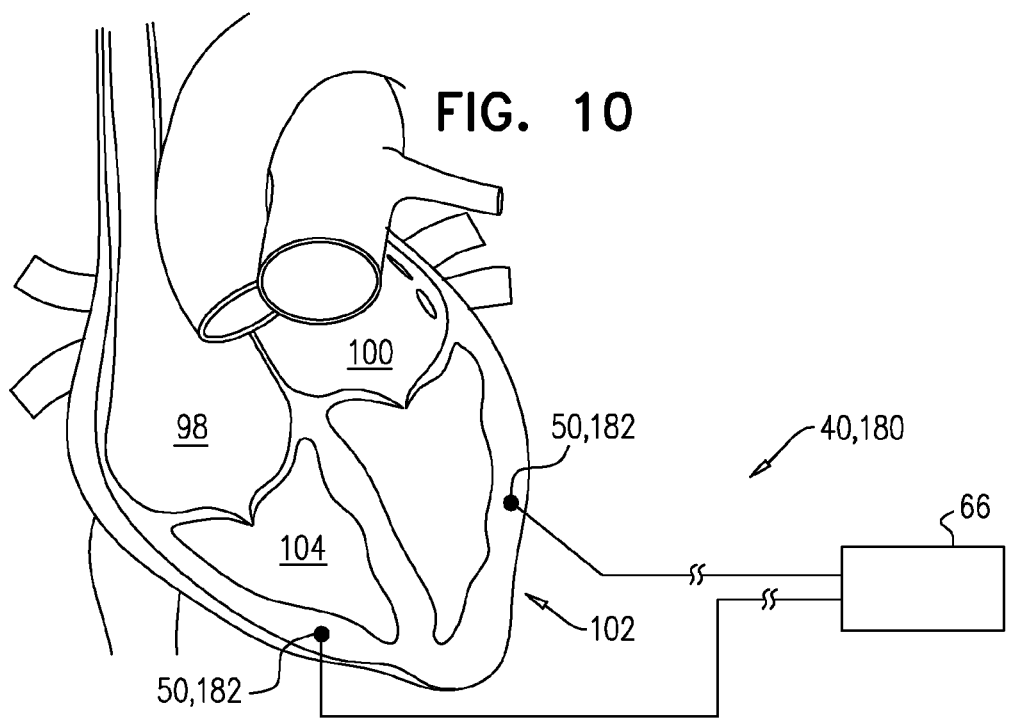

BLOOD FLOW CONTROL ELEMENT

FIELD OF THE INVENTION

Some applications of the present invention generally relate to medical apparatus. Specifically, some applications of the present invention relate to apparatus and methods for treating blood circulation disorders, particularly, congestive heart failure and associated symptoms.

BACKGROUND

Heart failure is a condition in which a problem with the structure or function of the heart impairs its ability to supply sufficient blood flow to meet the body's needs. The condition impairs quality of life and is a leading cause of hospitalizations and mortality in the western world. Treatment of heart failure is typically aimed at removal of precipitating causes, prevention of deterioration in cardiac function, and control of congestive state.

SUMMARY OF THE INVENTION

In some applications of the invention, an external device is used to detect one or more factors associated with a blood flow disorder of a subject. The external device transmits a signal, which is received by an implant. The implant is configured and positioned to alter a flow of blood of the subject, and alters the flow of blood of the subject at least in part responsively to the received signal. Typically, the apparatus is configured to operate only when the external device is located in proximity to the subject. For example, in some applications of the invention, the external device is located in, near or under a bed of the subject, such that detection of the factors by the external device, and detection of the signal by the implant, occur only when the subject is in the bed.

In some applications of the invention, the implant alters blood flow by variably occluding a blood vessel of the subject. In some applications of the invention, the implant functions by variably constricting a blood vessel of the subject. In some applications of the invention, the implant functions by providing a variable fistula between two blood vessels.

In some applications of the invention, the implant receives power wirelessly. In some applications, the implant receives power via electromagnetic induction. In some applications, the implant receives power via electromagnetic radiation.

There is therefore provided, in accordance with an application of the present invention, apparatus for altering blood flow of a subject, the apparatus including an implant, the implant including:

a receiver, configured to wirelessly receive a signal generated in response to a detection of a symptom of congestive heart failure (CHF);

an effector element, being disposable in a vicinity of a portion of a circulatory system of the subject; and a driver unit, coupled to the receiver, and configured to drive the effector element to reduce pulmonary blood flow, at least in part responsively to the signal.

In an application, the implant is configured to receive power from the signal.

In an application, the implant is configured to receive power via magnetic induction.

In an application, the effector element includes a tubular element, the tubular element being disposable between two hollow structures of the subject, and configured to provide fluid communication between the two hollow structures of the subject, and the driver unit is configured to reduce the pulmonary blood flow by altering a blood flow through the tubular element.

In an application, the driver unit is configured to alter the blood flow through the tubular element by altering a cross-sectional area of a lumen defined by the tubular element.

In an application, the apparatus includes a pump, and the driver unit is configured to alter the blood flow through the tubular element by driving the pump.

In an application, the driver unit is configured to reduce the pulmonary blood flow by driving the effector element to change a physical configuration thereof.

In an application, the driver unit is configured to drive the effector element to change the physical configuration thereof in a manner in which a final state of the reduction of the pulmonary blood flow is independent of a speed of the change of the physical configuration.

In an application, the effector element includes an occlusion structure, and the occlusion structure is disposable within the portion of the circulatory system of the subject.

In an application, the occlusion structure includes a balloon, and the driver unit is configured to reduce the pulmonary blood flow by changing a level of inflation of the balloon.

In an application, the effector element includes a cuff, the cuff being disposable around at least a part of a blood vessel of the subject, and the driver unit is configured to reduce the pulmonary blood flow by changing a cross-sectional area of a lumen defined by the cuff.

In an application, the effector element includes a fistula stent, the fistula stent being disposable in part in a wall of a first blood vessel of the subject and in part in a wall of a second blood vessel of the subject, and being configured to provide fluid communication between the first and second blood vessels, and the driver unit is configured to reduce the pulmonary blood flow by changing a cross-sectional area of a lumen defined by the fistula implant.

In an application, the effector element includes a tubular element, disposable in a septum between two heart chambers of the subject, and configured to provide fluid communication between the two heart chambers, and the driver unit is configured to reduce the pulmonary blood flow by changing a cross-sectional area of a lumen defined by the tubular element.

In an application, the effector element includes a cardiac valve-disruptor, the cardiac valve-disruptor being disposable in a cardiac valve of the subject.

In an application, the driver unit is configured to reduce the pulmonary blood flow by changing a configuration of the cardiac valve-disruptor.

There is further provided, in accordance with an application of the present invention, apparatus for altering blood flow of a subject, the apparatus including:

an external device, configured for placement outside of the subject, the external device including:
  a detector, configured to detect a factor associated with a disorder of the subject; and
  a control unit, couplable to the detector, configured to automatically generate a signal at least in part responsively to the detected factor; and
an implant, including:
  a receiver, configured to receive the signal;
  an effector element, being disposable in a vicinity of a portion of a circulatory system of the subject; and
  a driver unit, coupled to the receiver, and configured to drive the effector element to alter a blood flow in the portion of the circulatory system, at least in part responsively to the signal.

In an application, the detector is configured to detect a breathing-related factor of the subject.

In an application, the external device is configured to detect reclining of the subject, and to generate the signal at least in part responsively to the reclining of the subject.

In an application, the implant is configured to detect reclining of the subject, and the driver unit is configured to drive the effector element at least in part responsively to the reclining of the subject.

In an application, the control unit is configured to generate the signal as a radio frequency signal.

In an application, the control unit is configured to generate the signal as a magnetic signal.

In an application, the driver unit is configured to drive the effector element to inhibit the blood flow of the subject.

In an application, the driver unit is configured to drive the effector element to divert the blood flow of the subject.

In an application, the effector element includes a tubular element, the tubular element being disposable between two hollow structures of the subject, and configured to provide fluid communication between the two hollow structures of the subject, and the driver unit is configured to alter the blood flow by altering a blood flow through the tubular element.

In an application, the driver unit is configured to alter the blood flow through the tubular element by altering a cross-sectional area of a lumen defined by the tubular element.

In an application, the apparatus includes a pump, the driver unit is configured to alter the blood flow through the tubular element by driving the pump.

In an application, the driver unit is configured to alter the blood flow by driving the effector element to change a physical configuration thereof.

In an application, the driver unit is configured to drive the effector element to change the physical configuration thereof in a manner in which a final state of the alteration of the blood flow is independent of a speed of the change of the physical configuration.

In an application, the effector element includes an occlusion structure, and the occlusion structure is disposable within the portion of the circulatory system of the subject.

In an application, the occlusion structure includes a balloon, and the driver unit is configured to alter the blood flow by changing a level of inflation of the balloon.

In an application, the effector element includes a cuff, the cuff being disposable around at least a part of a blood vessel of the subject, and the driver unit is configured to alter the blood flow by changing a cross-sectional area of a lumen defined by the cuff.

In an application, the effector element includes a fistula stent, the fistula stent being disposable in part in a wall of a first blood vessel of the subject and in part in a wall of a second blood vessel of the subject, and being configured to provide fluid communication between the first and second blood vessels, and the driver unit is configured to alter the blood flow by changing a cross-sectional area of a lumen defined by the fistula implant.

In an application, the effector element includes a tubular element, disposable in a septum between two heart chambers of the subject, and being configured to provide fluid communication between the two heart chambers, and the driver unit is configured to alter the blood flow by changing a cross-sectional area of a lumen defined by the tubular element.

In an application, the effector element includes a cardiac valve-disruptor, the cardiac valve-disruptor being disposable in a cardiac valve of the subject.

In an application, the driver unit is configured to alter the blood flow by changing a configuration of the cardiac valve-disruptor.

In an application, the implant is configured to wirelessly receive power.

In an application, the implant is configured to receive power via magnetic induction.

In an application, the external device is configured to transmit power via magnetic induction.

In an application, the implant is configured to receive power via electromagnetic radiation transmitted by the external device, the implant further including a rectifying antenna.

In an application, the rectifying antenna is configured to receive power from the signal.

In an application, the rectifying antenna is configured to receive power from a second signal, and the control unit is configured to generate the second signal.

There is further provided, in accordance with an application of the present invention, a method for altering blood flow of a subject, the method including:

extracorporeally detecting a factor associated with a disorder of the subject;

automatically extracorporeally generating a signal, at least in part responsively to the detected factor;

intracorporeally detecting the signal; and automatically altering the blood flow of the subject, at least in part responsively to the signal.

In an application, the method further includes extracorporeally detecting reclining of the subject, automatically extracorporeally generating the signal includes automatically extracorporeally generating the signal at least in part responsively to the reclining of the subject.

In an application, the method further includes intracorporeally detecting reclining of the subject, automatically altering the blood flow of the subject includes automatically altering the blood flow of the subject at least in part responsively to the reclining of the subject.

In an application, extracorporeally detecting the factor includes extracorporeally detecting the factor while the subject is sleeping.

In an application, extracorporeally detecting the factor includes extracorporeally detecting a breathing-related factor of the subject.

In an application, altering the blood flow includes occluding a blood vessel of the subject.

In an application, altering the blood flow includes constricting a blood vessel of the subject.

In an application, altering the blood flow includes disrupting a function of a heart valve of the subject.

In an application, altering the blood flow includes inhibiting the blood flow of the subject.

In an application, intracorporeally detecting the signal includes wirelessly receiving power via the signal, using an implant, and automatically altering the blood flow includes powering the implant using the received power.

In an application, intracorporeally detecting the signal includes wirelessly receiving data via the signal, using an implant, and automatically altering the blood flow includes operating the implant responsively to the received data.

In an application, intracorporeally detecting the signal includes wirelessly receiving power via the signal, using an implant, and automatically altering the blood flow includes powering the implant using the received power, and intracorporeally detecting the signal includes wirelessly receiving data via the signal, using the implant, and automatically altering the blood flow includes operating the implant responsively to the received data.

In an application, generating the signal includes generating a radio frequency signal, and detecting the signal includes detecting the radio frequency signal.

In an application, generating the signal includes generating a magnetic signal, and detecting the signal includes detecting the magnetic signal.

In an application, altering the blood flow of the subject includes diverting the blood flow of the subject.

In an application, diverting the blood flow includes diverting blood from a first blood vessel of the subject to a second blood vessel of the subject.

In an application, diverting the blood flow includes diverting blood from a first heart chamber of the subject to a second heart chamber of the subject.

In an application, diverting the blood flow of the subject includes driving a pump.

In an application, diverting the blood flow includes adjusting a lumen of a tubular element.

In an application, diverting the blood flow includes diverting blood from a first heart chamber of the subject to a second heart chamber of the subject.

In an application, altering the blood flow of the subject includes adjusting a dimension of an effector element.

In an application, adjusting the dimension of the effector element includes adjusting a dimension of an occlusion structure, disposed within a blood vessel of the subject.

In an application, adjusting the dimension of the occlusion structure includes adjusting a level of inflation of a balloon.

In an application, adjusting the dimension of the effector element includes adjusting a cross-sectional area of a lumen of a cuff, disposed around at least a part of a blood vessel of the subject.

In an application, adjusting the dimension of the effector element includes adjusting a dimension of a heart valve-disruptor, the heart valve-disruptor being disposed in a vicinity of a valve of the heart.

In an application, adjusting the dimension of the effector element includes adjusting a cross-sectional area of a lumen of a tubular element.

In an application, adjusting the blood flow of the subject includes adjusting contractility of heart tissue of the subject.

In an application, adjusting contractility includes providing a non-excitatory signal to the heart tissue of the subject.

BRIEF DESCRIPTION OF THE DRAWINGS

FIGS. 6A-B are schematic illustrations of the implant, embodied as an occlusion implant, in accordance with some applications of the invention;

FIGS. 7A-B are schematic illustrations of the implant, embodied as a constriction implant, in accordance with some applications of the invention;

FIG. 8 is a schematic illustration of the implant, embodied as an aperture implant, in accordance with some applications of the invention;

FIG. 9 is a schematic illustration of the implant, embodied as a valve-disruptor implant, in accordance with some applications of the invention; and FIG. 10 is a schematic illustration of the implant, embodied as a contractility-control implant, in accordance with some applications of the invention.

DETAILED DESCRIPTION OF EMBODIMENTS

Figure 1:
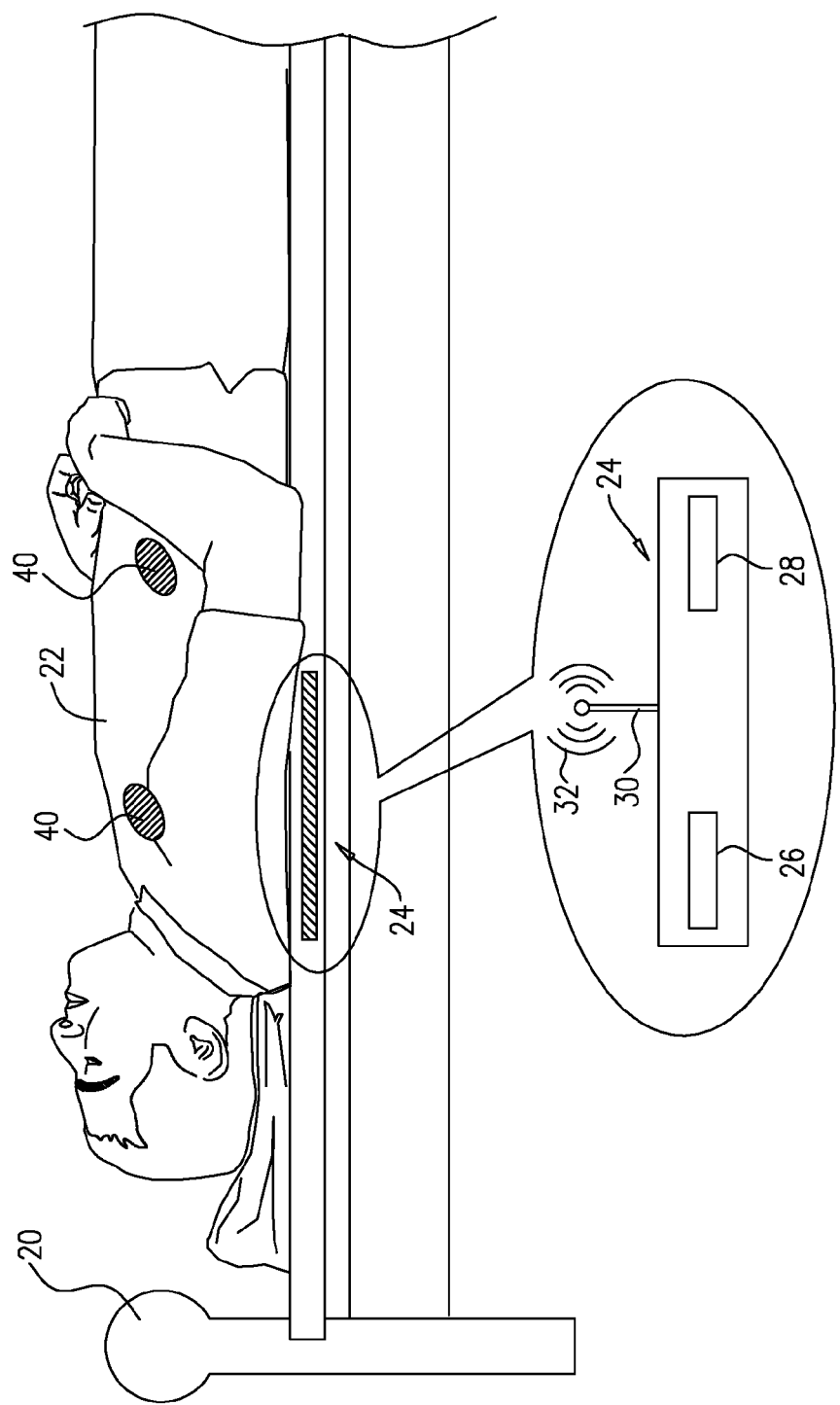
FIG. 1 is a schematic illustration of an implant implanted in a subject, and an external device in a vicinity of the subject, in accordance with some applications of the invention.

Reference is made to FIG. 1, which is a schematic illustration of a bed 20 and a subject 22 lying in the bed. Typically, the subject is sleeping. Typically, an external device 24 comprises a control unit 26, a sensor 28, and one or more antennas 30. The sensor senses one or more parameters of the subject. The parameters sensed are typically indicative of a pathology of the subject. For example, the sensor may detect breathing-related parameters of the subject that are indicative of an episode of, and/or deterioration in, congestive heart failure (CHF), and/or symptoms of CHF. External device 24 transmits one or more signals 32 to an implant 40, which is typically implanted in a vicinity of (e.g., in, or adjacent to) a portion of the circulatory system of the subject. Typically, signals 32 are transmitted at least in part in response to the sensed parameters. In some applications of the invention, signals 32 are alternatively or additionally transmitted according to a set program. In some applications of the invention, signals 32 are alternatively or additionally transmitted continuously, such that implant 40 receives the signals when the implant is within a range (e.g., less than 10 m, e.g., less than 5 m, e.g., less than 1 m) of the external device.

Implant 40 typically alters blood flow in at least the region of implantation and is described in more detail in accordance with FIGS. 4A-10. External device 24, in accordance with some applications of the present invention, is placed in proximity to the subject, under the subject, under or inside the subject's pillow or mattress, or on another part of the bed (e.g., on a bedpost). Alternatively, the external device can be placed anywhere near the subject, such that implant 40 receives signals 32 from the external device. For some applications of the invention, external device 24 is portable and/or wearable by the subject. External device 24 may be coupled to and/or disposed within an item of clothing (e.g., a hat; a belt) of the subject, or worn on a chest-band. The antennas 30 of external device 24 are typically configured to send signals 32 to the implant, as described hereinbelow.

External device 24 typically sends signals 32 to implant 40. At least in part responsively to signals 32, implant 40 alters the flow of blood in the region of implantation. For some applications, external device 24 sends signals 32 to implant 40 for a pre-determined length of time or in a particular pattern, or both. For some applications, periods of no stimulation by implant 40 are provided. In addition, external device 24 may be configured to detect reclining of the subject, and to only provide signals 32 to implant 40 when subject 22 is reclining (e.g., when the subject is sleeping). For example, in some applications, a sensor (e.g., sensor 28) is positioned in, on or under a mattress, and configured to detect the weight of the subject, and control unit 26 is configured to only transmit signals 32 when the weight of the subject is detected. Alternatively or additionally, as described hereinbelow (e.g., with reference to FIGS. 3A-B), in some applications, implant 40 may be configured to detect reclining of the subject, and to only respond to signals 32 when the subject is reclining (e.g., when the subject is sleeping).

Typically, signals 32 comprise data, and implant 40 receives the data and responds to the data. In some applications of the invention, external device 24 wirelessly powers implant 40 via wireless power 132, as described hereinbelow. When external device 24 wirelessly powers implant 40, wireless power 132 may comprise signals 32 and, thereby, comprise the data to which implant 40 typically responds. For some applications of the invention, the data may comprise an on/off command. For some applications of the invention, and as described hereinbelow (e.g., with reference to FIGS. 2A and 3A-B), implant 40 may be configured to only function when wireless power 132 is being received. In these applications, signals 32 may comprise only wireless power 132. That is, when signals 32 (i.e., wireless power 132) are received by implant 40, the implant is commanded (i.e., enabled) to function, and when signals 32 (i.e., wireless power 132) are not received by the implant, the implant is commanded not to function (i.e., is disabled from operating).

One or more of the implants are typically implanted into the subject in the vicinity of a blood vessel (e.g., in the blood vessel and/or on the blood vessel) of the subject. These one or more implants 40 may be configured to work in conjunction with other implants or independent of each other and/or external device 24. It is noted that the number of implants 40 in the illustration is by way of illustration and not limitation.

Closed-loop control (i.e., feedback control) is typically facilitated by continuous and/or repeated detection, by sensor 28, of the factors described hereinabove. In some applications of the invention, feedback is alternatively or additionally provided by subject 22 himself, or by other sensors such as additional feedback sensors (not shown). In addition, other sensors known in the art may be used to obtain feedback and to support feedback control of external device 24 and implant 40. Typically, sensing and responsive adjustment of blood flow is continuous and/or repeated over a duration of time (e.g., more than one hour, e.g., more than 4 hours, e.g., overnight). For severe conditions (e.g., bedridden subjects), sensing and responsive adjustment of blood flow may continue indefinitely.

Figure 2A:
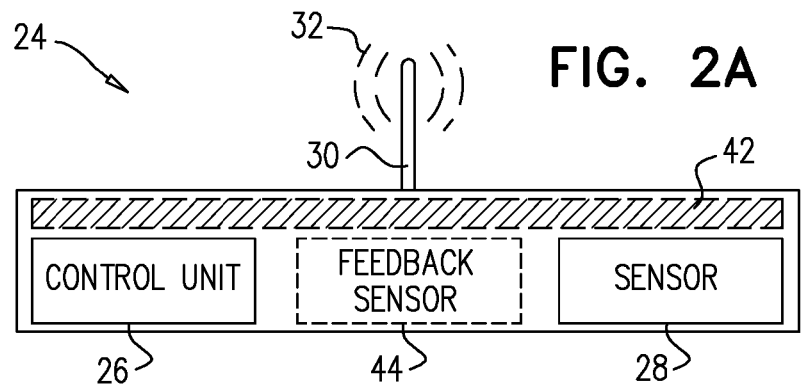
FIGS. 2A-C are schematic illustrations of the external device, in accordance with some applications of the invention.
Figure 2B:
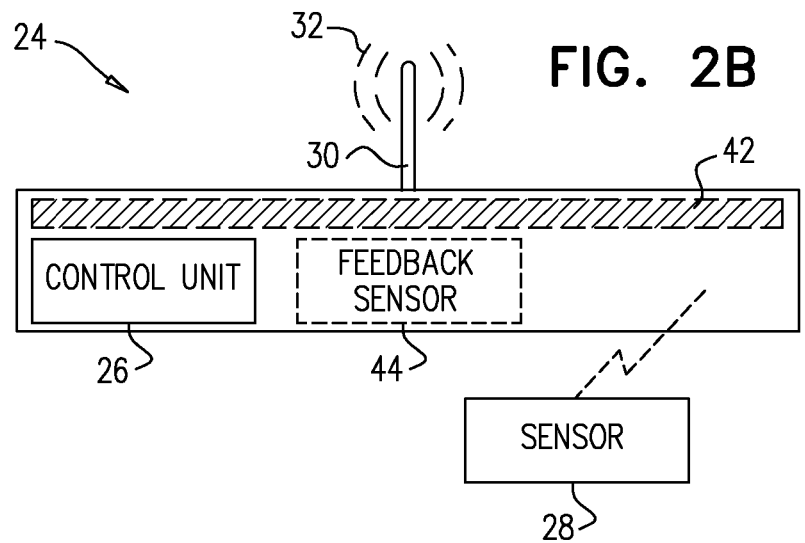
Figure 2C:
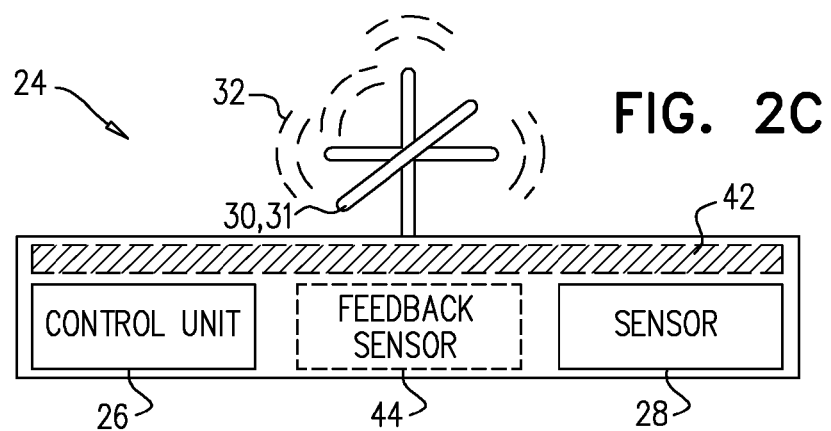

Reference is made to FIGS. 2A-C, which are schematic illustrations of external device 24, in accordance with some applications of the invention.

Reference is now made to FIG. 2A, which is a schematic illustration of external device 24, in accordance with an application of the invention. External device 24 comprises one or more antennas 30, a control unit 26, and one or more sensors 28. Sensor 28 typically detects one or more parameters of the subject, for example, breathing-related motions, breathing rate, heart rate, electrical activity, blood oxygenation, blood perfusion, sleep pattern and/or other indications of CHF.

Control unit 26 drives antenna 30 to transmit one or more signals 32, which is received by implant 40 when within an appropriate range. For example, the apparatus may be configured such that implant 40 is typically able to use signals 32 only when the subject is close to external device (e.g., within 10 m, e.g., within 5 m, e.g., within 1 m, e.g., when the subject is in bed). Typically, control unit 26 drives such signal transmission at least in part responsively to the one or more parameters detected by sensor 28. Alternatively or additionally, control unit 26 may drive signal transmission for a pre-determined and/or configurable length of time, or in a particular pattern. For some applications of the invention, signals 32 provide power to implant 40, as described hereinbelow. External device 24 may further comprise one or more additional feedback sensors 44, which detect one or more feedback parameters that indicate the efficacy and/or efficiency of the treatment applied by the implant 40. Alternatively or additionally, the feedback parameters may be the same as the parameters detected by sensor 28, in which case, feedback control is provided without the requirement for feedback sensor 44. Alternatively or additionally, feedback may be provided by the subject himself.

In some applications of the invention, external device 24 may further comprise one or more induction coils 42. Induction coils 42 are configured to supply power, via electromagnetic induction, to implant 40, in conjunction with one or more corresponding induction coils in the implant (not shown). This power may be consumed immediately by implant 40 and/or may be used to charge a power supply, as described hereinbelow.

Reference is now made to FIG. 2B. For some applications of the invention, sensor 28 is external to external device 24. For example, sensor 28 may be coupled to external device 24 by a wire, or may be wirelessly coupled to the external device. Externally-situated sensor 28 allows the sensor to be placed in a position that is suitable for detecting the parameters described hereinabove, whilst external device 24 is disposed in a position that is suitable for transmitting signals 32 to implant 40 and/or supplying wireless power to the implant.

Reference is now made to FIG. 2C. For some applications of the invention, antenna 30 comprises a multidirectional antenna 31 (e.g., a set of mutually-perpendicular antennas), such that signals 32 are receivable by implant 40, independently of the instantaneous orientation of implant 40 in subject 22 (e.g., due to the position of the subject on bed 20). Similarly, implant 40 may comprise a multidirectional antenna for receiving signals 32, generally independently of the orientation of the subject.

Figure 3A:
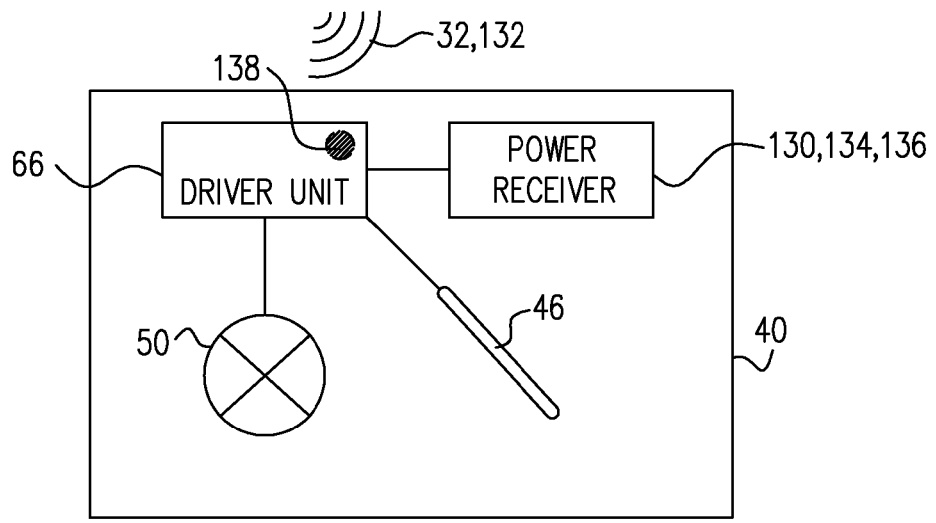
FIGS. 3A-B are schematic illustrations of the implant, comprising electrodes, in accordance with some applications of the invention.
Figure 3B:
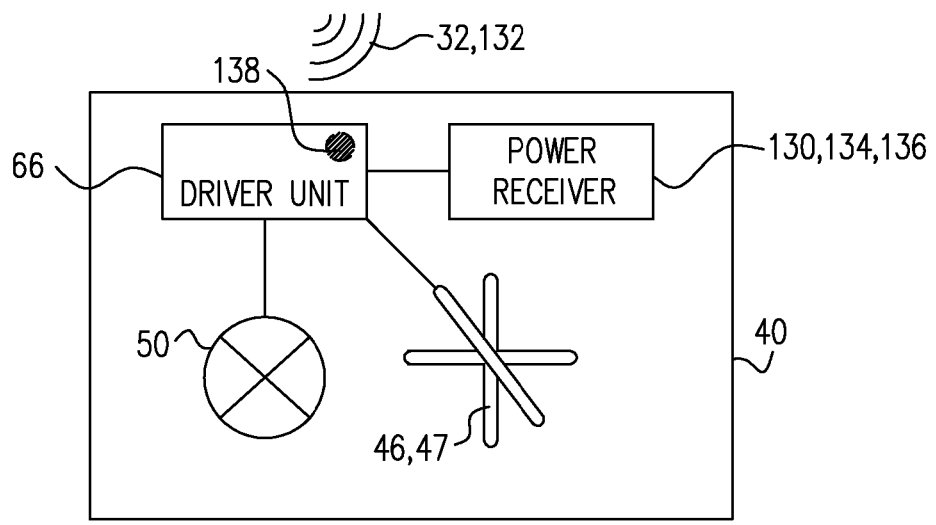

Reference is made to FIGS. 3A-B, which are schematic illustrations of implant 40, in accordance with some applications of the invention.

Reference is now made to FIG. 3A, which is a schematic illustration of implant 40, in accordance with some applications of the invention. Implant 40 typically comprises a driver unit 66, an antenna 46, and an effector element 50. Effector element 50 is typically electronically coupled to driver unit 66. The effector element may be disposed (i.e., implanted) adjacently to driver unit 66, or may be disposed at a different site. Implant 40 typically receives signals 32 from external unit 24, via antenna 46, and alters blood flow at least in part responsively to the signals, as described hereinbelow. Driver unit 66 typically comprises a power supply 138 (e.g., a battery and/or a capacitor). In some applications of the invention, implant 40 further comprises a power-receiver 130, which receives power wirelessly.

As described with reference to FIGS. 1-2, in some applications of the invention, implant 40 receives power from external unit 24 via electromagnetic induction. In such applications, power-receiver 130 comprises one or more induction coils 134, which typically receive power from induction coils 42 in external device 24.

In some applications of the invention, implant 40 may receive power via electromagnetic radiation (e.g., radio waves and/or microwaves), such as wireless power 132. In such applications of the invention, power-receiver 130 comprises a rectifying antenna (rectenna) 136, which converts wireless power 132 into electrical energy. In some applications of the invention, wireless power 132 may be a dedicated charging signal, transmitted by external device 24. Alternatively or additionally, wireless power 132 may include signals 32, which induce blood flow altering by implant 40. In some applications of the invention, implant 40 either does not comprise antenna 46, or does not comprise power-receiver 30. Rather, signals 32 and wireless power 132 are both received via either antenna 46, or by power-receiver 130.

Electrical energy supplied by power-receiver 130 typically charges power supply 138, such that implant 40 may function in the absence of continuous wireless power. Alternatively or additionally, electrical energy supplied by power-receiver 130 may be consumed by implant 42 as it is supplied. In some applications of the invention, element 50 only operates while wireless power 132 is being received by power-receiver 130.

Reference is now made to FIG. 3B. For some applications of the invention, antenna 46 comprises a multidirectional antenna 47 (e.g., mutually-perpendicular antennas), such that signals 32 from external device 24 are receivable by implant 40, independently of the orientation of subject 22 (e.g., the position of the subject on bed 20). Similarly, external device 24 may comprise a multidirectional antenna for receiving signals 32, independently of the orientation of the subject.

Reference is again made to FIGS. 3A-B. In some applications, implant 40 may be configured to detect reclining of the subject, and/or to only respond to signals 32 when the subject is reclining (e.g., when the subject is sleeping). For example, implant 40 may comprise an orientation sensor, such as a gyroscope (e.g., as is known in the cellular telephone art), and driver unit 66 may be configured to drive effector element 50 only when the subject is reclining (e.g., when the subject is sleeping).

The applications of the invention described with reference to FIGS. 1-3 may be combined with those applications described hereinbelow, including those described with reference to FIGS. 4A-10.

Reference is made to FIGS. 4A-10, which are schematic illustrations of implant 40, in accordance with respective applications of the invention. For clarity, only driver unit 66 and effector element 50 of implant 40 are shown in these figures.

Figure 4A:
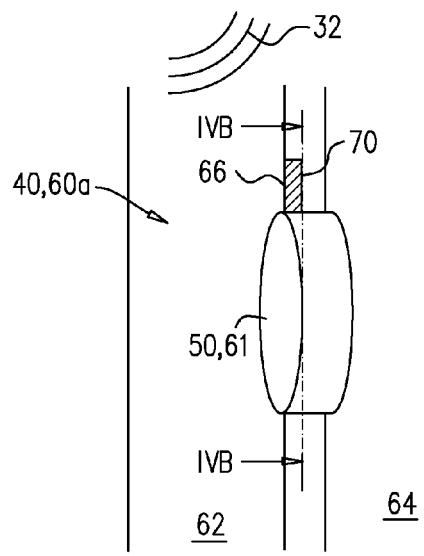
FIGS. 4A-B are schematic illustrations of the implant, embodied as a fistula implant, in accordance with some applications of the invention.
Figure 4B:
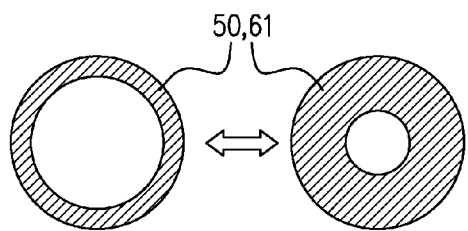

Reference is made to FIGS. 4A-B, which are schematic illustrations of implant 40, embodied as an adjustable fistula implant 60a, in accordance with some applications of the invention.

Reference is now made to FIG. 4A. Effector element 50 of fistula implant 60a typically comprises a tubular element 61, which is shaped to define a lumen and can facilitate communication between two hollow structures, such as a first blood vessel 62 and a second blood vessel 64. Typically, fistula implant is implanted such that it provides communication between an artery and a vein, whereby arterial blood can pass through fistula implant 60a into the venous system. For example, fistula implant 60a may be implanted between the iliac artery and iliac vein of the subject, or between another artery and vein of the subject. At least in part responsively to signals 32 from external unit 24, driver unit 66 drives effector element 50 to alter blood flow through tubular element 61. For example, driver unit 66 may drive an adjustment of a dimension of tubular element 61, such as the cross-sectional area of the lumen of the tubular element.

Reference is now made to FIG. 4B, which is a schematic illustration of fistula implant 60a showing a cross section of tubular element 61, illustrated in FIG. 4A. This figure more clearly illustrates the adjustability of a dimension of implant 40, that is described with reference to FIG. 4A. Adjustment of the cross-sectional area of the lumen defined by tubular element 61 alters blood flow through the tubular element. For example, in response to detection of a phenomenon related to CHF, driver unit 66 may increase the cross-sectional area of the lumen, to increase blood flow through the tubular element.

Mechanisms by which driver unit 66 may drive adjustment of the cross-sectional area of tubular element 61 include, but are not limited to, electromechanical control (e.g., the use of an electroactive polymer) and hydraulic control, and may comprise the use of a servo drive.

Figure 5:
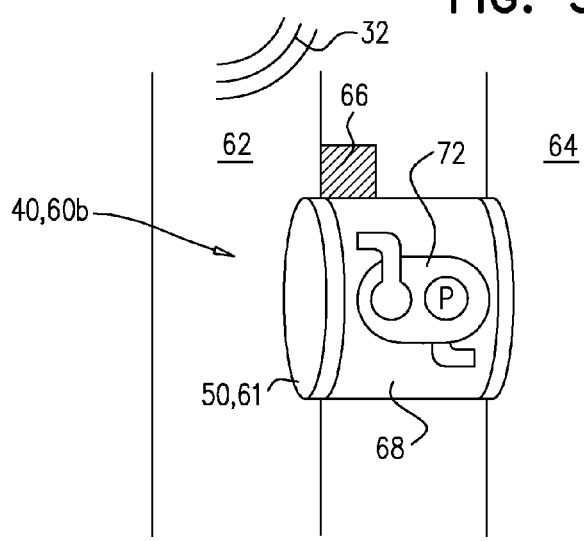
FIG. 5 is a schematic illustration of the implant, embodied as a fistula implant, in accordance with some applications of the invention.

Reference is now made to FIG. 5, which is a schematic illustration of fistula implant 60b, according to an application of the invention. In this application of the invention, tubular element 61 comprises or is coupled to a conduit 68. The lengthened implant allows a fistula to be maintained between the two hollow structures (i.e., the blood vessels) when the structures are spaced further apart. The rigidity of conduit 68 may be adapted for use in various situations. Alternatively or additionally to blood flow control via adjustment of the lumen, implant 60b may comprise a pump 72, whereby blood flow is controlled by controlling the rate of pumping. For example, in response to detection of a phenomenon related to CHF, driver unit 66 may drive pump 72 to increase blood flow through implant 60b. Although pump 72 is described with reference to FIG. 5, it may be combined with other applications of the invention, for example the applications described with reference to FIGS. 4A-B.

Reference is again made to FIGS. 4A-5. It is to be noted that although fistula implants 60a and 60b are shown providing fluid communication between two blood vessels of the subject, the scope of the present application includes fistula implants that provide communication between other hollow structures of the subject.

Reference is made to FIGS. 6A-B, which are schematic illustrations of implant 40, embodied as an adjustable occlusion implant 90, in accordance with an application of the invention.

Reference is now made to FIG. 6A. The effector element 50 of occlusion implant 90 comprises an occlusion element that has an adjustable dimension. Typically, the occlusion element comprises a balloon 92, and the adjustable dimension is a cross-sectional area of the balloon. Typically, the cross-sectional area of the balloon is adjustable via inflation of the balloon. Implant 90 is disposed in the lumen of a blood vessel which, in this application of the invention, is superior vena cava 94. Additionally or alternatively, implant is disposed in the lumen of another blood vessel such as inferior vena cava 96. Inflation of balloon 92 increases occlusion of the blood vessel in which the balloon is disposed. Driver unit 66 receives signals 32 from external device 24 and, at least in part responsively to the signals, alters blood flow by adjustment of the level of inflation of balloon 92. For example, in response to detection of a phenomenon related to CHF, driver unit 66 may increase the inflation of balloon 92, to reduce blood flow through superior vena cava 94 and into right atrium 98. Typically, balloon 92 is inflated with saline. In FIG. 6A, balloon 92 is shown in a deflated state.

Reference is now made to FIG. 6B, which is a schematic illustration of occlusion implant 90 with balloon 92 in an inflated state. In this state, balloon 92 at least partly occludes superior vena cava 94, reducing blood flow into right atrium 98. Reduction of blood flow into right atrium 98 reduces the congestion of the lungs associated with CHF. Other uses of occlusion implant 90 may be alternatively or additionally employed, in accordance with applications of the invention.

Reference is now made to FIGS. 7A-B, which are schematic illustrations of implant 40, embodied as an adjustable constriction implant 110, in accordance with an application of the invention.

Reference is now made to FIG. 7A. The effector element of constriction implant 110 comprises a constriction element that has an adjustable dimension. Typically, the constriction element comprises an inflatable cuff 112, and the adjustable dimension is a cross-sectional area of a lumen defined by the cuff. Typically, the cross-sectional area of the lumen is adjustable via inflation of the cuff. Implant 110 is disposed around a blood vessel which, in this application of the invention, is superior vena cava 94. Additionally or alternatively, implant 110 may be disposed around another blood vessel such as inferior vena cava 96. Inflation of cuff 112 constricts the blood vessel around which the cuff is disposed. Driver unit 66 receives signals 32 from external device 24 and, at least in part responsively to the signals, alters blood flow by adjustment of the level of inflation of cuff 112. For example, in response to detection of a phenomenon related to CHF, driver unit 66 may increase the inflation of cuff 112, to reduce blood flow through superior vena cava 94 and into right atrium 98. Typically, inflatable cuff 112 is inflated with a fluid (e.g., saline). In this figure, cuff 112 is in a deflated state.

Reference is now made to FIG. 7B, which is a schematic illustration of occlusion implant 110 with cuff 112 in an inflated state. In this state, cuff 112 at least partly constricts superior vena cava 94, reducing blood flow into right atrium 98 of heart 102 of the subject. Other uses of constriction implant 110 may be alternatively or additionally employed, in accordance with applications of the invention.

Reference is made to FIG. 8, which is a schematic illustration of implant 40, embodied as an adjustable aperture implant 150, in accordance with an application of the invention. Effector element 50 of aperture implant 150 typically comprises a tubular element 152, which is shaped to define a lumen. Tubular element 152 is configured to facilitate communication between two hollow structures of the subject. Tubular element 152 is typically implanted in an interatrial septum of the subject, so as to facilitate communication between a right atrium 98 and a left atrium 100 of heart 102 of the subject. That is, tubular element 152 provides a shunt between the two atria. At least in part responsively to signals 32 from external unit 24, driver unit drives effector element 50 to alter blood flow through tubular element 152. Typically, driver unit 66 drives tubular element 152 to adjust a dimension thereof. For example, driver unit 66 may cause an increase of the cross-sectional area of the lumen of tubular element 152, in response to detection of a phenomenon related to CHF, as described with reference to FIGS. 4A-B, mutatis mutandis. Increasing the cross-sectional area of the lumen of tubular element 152 is hypothesized to increase inter-atrial shunting, thereby reducing the congestion of the lungs associated with CHF. Other uses of adjustable aperture implant 150 may be alternatively or additionally employed, in accordance with applications of the invention.

Reference is now made to FIG. 9, which is a schematic illustration of implant 40, embodied as an adjustable valve-disruptor implant 160. Valve-disruptor implant 160 is typically implanted at a native heart valve such as a tricuspid valve 108 of the subject. At least in part responsively to signals 32 from external unit 24, driver unit drives effector element 50 to adjust a level of interference with leaflets 106 of the native valve. In some applications of the invention, driver unit 66 drives effector element 50 of valve-disruptor implant 160 to adjust a dimension thereof. In some applications of the invention, effector element 50 of valve-disruptor implant 160 comprises one or more wire loops 162 and a sleeve 164, slidably coupled to the wire loops. Wire loops 162 typically have an expanded configuration in which the wire loops interfere with leaflets 106 to a relatively high degree, and a constricted configuration in which the wire loops interfere with leaflets 106 to a relatively low degree. The degree of expansion of wire loops 162 is controlled by the sliding of sleeve 164 over the wire loops. Driver unit 66 thereby adjusts blood flow through the heart valve by sliding sleeve 164 over wire loops 162, at least in part responsively to signals 32 from external unit 24. For example, in response to detection of a phenomenon related to CHF, driver unit 66 may allow wire loops 162 to expand, increasing their interference with leaflets 106, thereby increasing regurgitation. Increased tricuspid valve regurgitation is hypothesized to reduce the congestion of the lungs associated with CHF. For some applications, valve-disruptor implant 160 is constructed using effector elements 50 other than wire loops and a sheath, in accordance with applications of the invention.

Reference is now made to FIG. 10, which is a schematic illustration of implant 40, embodied as a contractility-control implant 180. Effector element 50 of contractility-control implant 180 typically comprises one or more electrodes 182, electrically coupled to driver unit 66. Electrodes 102 are typically coupled to respective cardiac sites, facilitating electrical stimulation of heart 102 of the subject, by driver unit 66. Driver unit 66 is typically configured to provide a non-excitatory signal to the heart, at least in part responsively to signals 32 from external unit 24. For example, in response to detection of a phenomenon related to CHF, driver unit 66 may provide the non-excitatory signal to the heart. The non-excitatory signal is hypothesized to increase the contractility of cardiac muscle, and thereby increase the power and/or volume of each stroke of the heart. Typically, but not necessarily, the non-excitatory signal is provided during refractory periods in the cardiac cycle. Further typically, the non-excitatory signal comprises a series of closely-paced pulses. The non-excitatory signal supplied by contractility-control implant 180 is hypothesized to increase the contractility of cardiac muscle, thereby increasing the velocity and/or power of beats of the heart. For some applications, apparatus and methods described in U.S. Pat. No. 7,167,748 to Ben-Haim et al., which is incorporated herein by reference, are utilized in combination with the apparatus and methods described herein, in order to produce increased cardiac contractility.

In some applications of the invention, driver unit 66 is further configured to detect natural cardiac depolarization events, and the non-excitatory signal is provided at least in part responsively to the detected events.

In some applications of the invention, excitatory signals (e.g., pacing signals) are further provided to the heart of the subject. For example, contractility-control implant 180 may be used in combination with a cardiac pacemaker, or a single implant may provide both contractility-control and pacing, via non-excitatory and excitatory signals, respectively, at least in part responsively to signals 32 from external unit 24. Other uses of contractility-control implant 180 may be alternatively or additionally employed, in accordance with applications of the invention.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for altering blood flow of a subject, the apparatus comprising:
    an external device, configured for placement outside of the subject, the external device comprising:
        a detector, configured to detect a factor associated with a disorder of the subject; and a control unit, couplable to the detector, configured to automatically generate a signal at least in part responsively to the detected factor; and an implant, comprising:
  a receiver, configured to receive the signal;
  an effector element, being disposable in a vicinity of a portion of a circulatory system of the subject; and
  a driver unit, coupled to the receiver, and configured to drive the effector element to divert a blood flow in the portion of the circulatory system, at least in part responsively to the signal.

2. The apparatus according to claim 1, wherein the detector is configured to detect a breathing-related factor of the subject.

3. The apparatus according to claim 1, wherein the external device is configured to detect reclining of the subject, and to generate the signal at least in part responsively to the reclining of the subject.

4. The apparatus according to claim 1, wherein the control unit is configured to generate the signal as a radio frequency signal.

5. The apparatus according to claim 1, wherein the driver unit is configured to drive the effector element to inhibit the blood flow of the subject.

6. The apparatus according to claim 1, wherein the effector element comprises a tubular element, the tubular element being disposable between two hollow structures of the subject, and configured to provide fluid communication between the two hollow structures of the subject, and wherein the driver unit is configured to alter the blood flow by altering a blood flow through the tubular element.

7. The apparatus according to claim 1, wherein the driver unit is configured to alter the blood flow by driving the effector element to change a physical configuration thereof.

8. The apparatus according to claim 7, wherein the driver unit is configured to drive the effector element to change the physical configuration thereof in a manner in which a final state of the alteration of the blood flow is independent of a speed of the change of the physical configuration.

9. The apparatus according to claim 7, wherein the effector element comprises a fistula stent, the fistula stent being disposable in part in a wall of a first blood vessel of the subject and in part in a wall of a second blood vessel of the subject, and being configured to provide fluid communication between the first and second blood vessels, and wherein the driver unit is configured to alter the blood flow by changing a cross-sectional area of a lumen defined by the fistula implant.

10. The apparatus according to claim 7, wherein the effector element comprises a tubular element, disposable in a septum between two heart chambers of the subject, and being configured to provide fluid communication between the two heart chambers, and wherein the driver unit is configured to alter the blood flow by changing a cross-sectional area of a lumen defined by the tubular element.

11. The apparatus according to claim 1, wherein the implant is configured to wirelessly receive power.

12. A method for altering blood flow of a subject, the method comprising:
  extracorporeally detecting a factor associated with a disorder of the subject while the subject is sleeping;
  automatically extracorporeally generating a signal, at least in part responsively to the detected factor;
  intracorporeally detecting the signal; and
  automatically altering the blood flow of the subject, at least in part responsively to the signal.

13. The method according to claim 12, further comprising extracorporeally detecting reclining of the subject, wherein automatically extracorporeally generating the signal comprises automatically extracorporeally generating the signal at least in part responsively to the reclining of the subject.

14. The method according to claim 12, wherein extracorporeally detecting the factor comprises extracorporeally detecting a breathing-related factor of the subject.

15. The method according to claim 12, wherein altering the blood flow comprises at least partially occluding a blood vessel of the subject.

16. The method according to claim 12, wherein altering the blood flow comprises inhibiting the blood flow of the subject.

17. The method according to claim 12, wherein intracorporeally detecting the signal comprises wirelessly receiving power via the signal, using an implant, and wherein automatically altering the blood flow comprises powering the implant using the received power.

18. The method according to claim 12, wherein intracorporeally detecting the signal comprises wirelessly receiving data via the signal, using an implant, and wherein automatically altering the blood flow comprises operating the implant responsively to the received data.

19. The method according to claim 12, wherein generating the signal comprises generating a radio frequency signal, and wherein detecting the signal comprises detecting the radio frequency signal.

20. The method according to claim 12, wherein altering the blood flow of the subject comprises diverting the blood flow of the subject.

21. The method according to claim 20, wherein diverting the blood flow comprises diverting blood from a first blood vessel of the subject to a second blood vessel of the subject.

22. The method according to claim 20, wherein diverting the blood flow comprises diverting blood from a first heart chamber of the subject to a second heart chamber of the subject.

23. Apparatus for altering blood flow of a subject, the apparatus comprising:
  an external device, configured for placement outside of the subject, the external device comprising:
    a detector, configured to detect a factor associated with a disorder of the subject; and
    a control unit, couplable to the detector, configured to automatically generate a signal at least in part responsively to the detected factor; and
  an implant, comprising:
    a receiver, configured to receive the signal;
    an effector element, being disposable in a vicinity of a portion of a circulatory system of the subject, and comprising an occlusion structure disposable within the portion of the circulatory system; and
    a driver unit, coupled to the receiver, and configured to drive the effector element to alter a blood flow in the portion of the circulatory system:
      at least in part responsively to the signal, and
      by driving the effector element to change a physical configuration thereof.

\* \* \* \* \*